US006462003B1

(12) United States Patent
Shimosato et al.

(10) Patent No.: US 6,462,003 B1
(45) **Date of Patent: *Oct. 8, 2002**

(54) TRANSPARENT SOLID SOAP AND TRANSPARENT SOAP MATERIAL

(75) Inventors: Isao Shimosato; Masanori Okada, both of Yokohama (JP)

(73) Assignee: Pola Chemical Industries, Inc., Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/619,367

(22) Filed: Jul. 19, 2000

Related U.S. Application Data

(63) Continuation of application No. 09/297,593, filed as application No. PCT/JP97/03137 on Sep. 5, 1997.

(51) Int. Cl.[7] .................................................. A61K 7/50

(52) U.S. Cl. ....................... 510/147; 510/152; 510/153; 510/154; 510/499

(58) Field of Search ................................ 510/152, 153, 510/154, 156, 147, 141

(56) References Cited

U.S. PATENT DOCUMENTS 1,847,437 A 3/1932 Moscowitz
4,297,230 A 10/1981 Rasser
5,728,663 A * 3/1998 Lambino .................... 510/152

FOREIGN PATENT DOCUMENTS

| | | | |
|---|---|---|---|
| EP | 0 335 026 | | 10/1989 |
| JP | 60-188500 | * | 9/1985 |
| JP | 63-275700 | * | 11/1988 |

* cited by examiner

*Primary Examiner*—Necholus Ogden
(74) *Attorney, Agent, or Firm*—Knobbe, Martens, Olson & Bear, LLP

(57) ABSTRACT

A transparent solid soap or transparent soap material which comprises mainly of a salt of the fatty acid, is obtained by saponifying fatty acid or animal/vegetable oil with alkali, wherein 1) the alkali is sodium hydroxide and organic amine, and a molar ratio of sodium hydroxide to organic amine is from 1:0.8 to 1:2, and
2) a quantity of the alkali is 2 to 3 saponifying equivalents to the fatty acid or the animal/vegetable oil.

The transparent solid soap and the transparent soap material according to the present invention can be easily produced without requiring a fine control of moisture content, and a maturing period till reduction in weight is settled, and, besides, good in stabilities of transparency and of weight with a passage of time.

10 Claims, No Drawings

TRANSPARENT SOLID SOAP AND TRANSPARENT SOAP MATERIAL

This is a continuation of U.S. Ser. No. 09/297,593, filed May 3, 1999 which is the U.S. National Phase under 35 U.S.C. §371 of International Application PCT/JP97/03137, filed Sep. 5, 1997.

TECHNICAL FIELD

The present invention relates generally to a transparent solid soap and a transparent soap material and, more particularly, to a transparent solid soap and a transparent soap material which can be easily produced without requiring a fine control of a water content and a maturing period till reduction in weight is settled and, besides, exhibit high stabilities of transparency and weight with a passage of time.

BACKGROUND ARTS

A transparent soap is visually beautiful and excellent in terms of safety and detergency, and is therefore widely used as a detergent. Generally, the transparent soap is mixed with a moisture absorbing component as an indispensable component such as polysaccharide, and the like in order to create the transparency and mixed, in addition, with a volatile component such as ethanol, and the like.

The transparent solid soap, however, declines in terms of the transparency on the contrary when the moisture component absorbs the moisture content, and it is therefore required that fine control of the water content be precisely made by a hot roll while monitoring the transparency and the water content. Further, when mixed with the volatile component, the volatile component volatilizes, resulting in a decrease in weight. Hence, a maturing period as long as several weeks through several months is needed till the decrease in weight is settled. Namely, it is quite troublesome to execute the control so as to exhibit high transparency and high stabilities of transparency and of weight with a passage of time in terms of manufacturing the transparent solid soap.

Moreover, if processed as a soap with a stripe pattern by use of a conventional transparent soap material together with other opaque soap materials, the transparency of the transparent soap portion is spoiled by the moisture content contained in the opaque soap, which leads to a drawback in which the stripe pattern becomes blurred. Furthermore, some of the actually used transparent solid soaps are mixed with sorbitol defined as polysaccharide in order to enhance the transparency. Sorbitol is, however, crystal-deposited as the time elapses enough to make the transparent soap cloudy, and it happened often that the stability of transparency with the passage of time might be spoiled.

Under such circumstances, there has been demanded a transparent soap that can be easily produced without requiring the fine control of the water content and the maturing period and, besides, exhibits the high stabilities of transparency and of weight with the passage of time.

On the other hand, it has already practiced that the transparent solid soap is mixed with organic amine such as triethanolamine, but high-concentration mixing was not carried out. Further, it was not absolutely known that the transparent solid soap and the transparent soap material, which can be easily produced and exhibit the high stability, are obtained by mixing with organic amine such as triethanolamine with the high concentration.

DISCLOSURE OF THE INVENTION

It is an object of the present invention, which was contrived under such circumstances, to provide a transparent solid soap and a transparent soap material with a decreased labor for fine control of a moisture content, which can be easily produced without requiring a maturing period till reduction in weight is settled and are good in terms of stabilities of transparency and of weight with a passage of time.

Under such circumstances, as a result of wholeheartedly having made studies over and over to obtain the transparent solid soap and the transparent soap material that are easy to produce and exhibit a good stability, the present inventors obtained the soap that remains transparent even when polysaccharide and alcohol are not required to be indispensable components, which involves using sodium hydroxide and organic amine at a predetermined ratio as alkali used for saponification and letting a quantity of alkali with respect to fatty acid be a predetermined saponifying equivalent, and found out that this transparent soap is easy to produce and exhibits a good stability, thus having completed the present invention.

Namely, the present invention relates to a transparent solid soap obtained by saponifying fatty acid or animal/vegetable oil with alkali, which comprises mainly a salt of fatty acid, wherein 1) the alkali is sodium hydroxide and organic amine, and a molar ratio of the sodium hydroxide to the organic amine is from 1:0.8 to 1:2, and
2) a quantity of the alkali is 2 to 3 saponifying equivalents to the fatty acid or the animal/vegetable oil.

It is particularly preferable that the organic amine is triethanolamine.

Further, the present invention relates to a transparent soap material obtained by saponifying fatty acid or animal/vegetable oil with alkali, which comprises mainly a salt of fatty acid, wherein 1) the alkali is sodium hydroxide and organic amine, and a molar ratio of the sodium hydroxide to the organic amine is from 1:0.8 to 1:2, and
2) a quantity of the alkali is 2 to 3 saponifying equivalents to the fatty acid or the animal/vegetable oil.

The transparent soap material according to the present invention can be solidified as a pellet.

Further, the present invention relates to a transparent solid soap obtained by molding the above transparent soap material.

Note that the term "transparent" implies a state of being substantially clear with slight turbidity as well as implying that a transmissivity of the visible light is approximately 25% or above. Moreover, the term "transparent" is not limited to achromatic transparency.

As for a distinction between the "transparent solid soap" and the "transparent soap material", the "transparent solid soap" is conceptualized as being molded and solidified into a usable form, while the "transparent soap material" is conceptualized as a state before being molded into the transparent solid soap. Further, according to the present invention, the "transparent solid soap" includes a soap molded into the usable form, a portion of which is transparent.

The term "saponifying equivalent" means a minimum alkali quantity needed for transforming all of fatty acid or animal/vegetable oil into a salt of fatty acid, i.e., into a soap, and a quantity thereof should be regarded as 1 saponifying equivalent.

The transparent solid soap and the transparent soap material according to the present invention are the transparent soap in which polysaccharide such as sorbitol or alcohol such as ethanol are not used as indispensable components. Accordingly, it is rare to generate turbidity caused by moisture absorption or crystal depositon, and the like, which happen on a soap comprising the polysacchride, and excellent in terms of a stability of transparency with a passage of time. Moreover, the transparent solid soap and the transparent soap material according to the present invention are easy to produce for the reason that a labor for controlling a moisture content is reduced because of moisture absorbing components such as polysaccharide being not indispensable, and that a maturing period till a reduction in weight is settled after a volatile component such as alcohol has come to an equilibrium, is not indispensable.

The present invention will hereinafter be described in detail.

(1) Transparent Solid Soap of the Present Invention

A transparent solid soap of the present invention is obtained by saponifying fatty acid or animal/vegetable oil with alkali, which comprises mainly a salt of fatty acid, wherein 1) the alkali is sodium hydroxide and organic amine, and a molar ratio of the sodium hydroxide to the organic amine is from 1:0.8 to 1:2, and
2) a quantity of the alkali is 2 to 3 saponifying equivalents to the fatty acid or the animal/vegetable oil.

Herein, diethanolamine, triethanolamine, triethylamine, trimethylamine and diethylamine, and the like are exemplified as preferable organic amine. Among these kinds of amine, triethanolamine is particularly preferable. One kind of organic amine may be solely used, or tow or more kinds of amine may also be employed in combination.

The alkali quantity in saponifying the fatty acid or the animal/vegetable oil with the alkali is preferably 2 to 3 saponifying equivalents, more preferably, 2.1 to 2.9 saponifying equivalents and, much more preferably, 2.2 to 2.7 saponifying equivalents with respect to the fatty acid or the animal/vegetable oil.

Note that the term "saponifying equivalent" in the present invention means a minimum alkali quantity required for transforming all of the fatty acid or the animal/vegetable oil into a salt of fatty acid, viz., into the soap, and a quantity thereof should be regarded as 1 saponifying equivalent. The alkali quantity corresponding to 1 saponifying equivalent, for example, can be obtained as the alkali quantity necessary for neutralizing the acid derived from the fatty acid, calculating the acid quantity from the weight and the molecular weight of the fatty acid.

Further, a ratio of the sodium hydroxide to the organic amine is preferably from 1:0.8 to 1:2, more preferably from 1:0.9 to 1:1.9 and, still more preferably, from 1:1 to 1:1.8 in molar ratio.

The fatty acid or the animal/vegetable oil used for the transparent solid soap according to the present invention may be those generally employed as fundamental sources. As the fatty acid, there can be specifically exemplified stearic acid, lauric acid, myristic acid, palmitic acid and behenic acid and the like. The fatty acid, whether synthetic or natural, may be available. Further, as the animal/vegetable oil, specifically, beef tallow, coconut oil and hydrogenated coconut oil, and the like, which is previously hydrolyzed into the fatty acid, may be used or may be used intact.

Further, a quantity of the fatty acid prepared as a raw material into the transparent solid soap according to the present invention, i.e., a preparing quantity of the fatty acid, is preferably from 30% to 60% by weight, more preferably from 35% to 57% by weight and, much more preferably, from 37% to 55% by weight. Moreover, a preparing quantity of triethanolamine is from 30% to 50% by weight, more preferably from 31% to 47% by weight, and even more preferably from 32% to 45% by weight. Furthermore, a preparing quantity of sodium hydroxide is preferably from 5% to 10% by weight, more preferably from 5.5% to 9.5% by weight, and much more preferably from 6% to 9% by weight.

In the transparent solid soap according to the present invention, if in such a range as not to spoil the effects of the present invention, there can be optional components generally used for the soap in addition to the indispensable components described above. As the above optional components, there may be exemplified, e.g., antioxidant such as BHT, chelating agent such as EDTA and hydroxyethane diphosphonic acid, antiseptic agent such as methylparaben, coloring matters, pigments, fine particles, mica titanes with interference colors, pearl agent such as mica titanes, perfume, surface active agent such as POE added sodium alkylsulfate, and monovalent or polyvalent alcohol or polysaccharide such as ethanol, glycerine, white saccharide, maltitol, sorbitol and honey and the like.

Note that the transparent solid soap according to the present invention is mixed with the coloring matters, the pigments, the fine particles, the mica titanes with interference colors or the pearl agent as the above optional component, whereby the soap can, though the transparency might be spoiled to some extent depending on an addition quantity, become highly lustrous and conspicuous in color.

The transparent solid soap according to the present invention can be manufactured by an ordinary transparent solid soap manufacturing method. For example, the transparent solid soap can be manufactured by a frame kneading method of saponifying the fatty acid or the animal/vegetable oil with alkali, melting a mixture by heating that are mixed with other components as the necessity arises, pouring the mixture into a mold and solidifying it by cooling.

(2) Transparent Soap Material of the Present Invention

A transparent soap material of the present invention is obtained by saponifying fatty acid or animal/vegetable oil with alkali, which comprises mainly a salt of fatty acid, wherein 1) the alkali is sodium hydroxide and organic amine, and a molar ratio of the sodium hydroxide to the organic amine is from 1:0.8 to 1:2, and
2) a quantity of the alkali is 2 to 3 saponifying equivalents to the fatty acid or the animal/vegetable oil.

Herein, diethanolamine, triethanolamine, triethylamine, trimethylamine and diethylamine, and the like are exemplified as preferable organic amine. Among these kinds of amine, triethanolamine is particularly preferable. One kind of organic amine may be solely used, or tow or more kinds of amine may also be employed in combination.

The alkali quantity in saponifying the fatty acid or the animal/vegetable oil with the alkali is preferably 2 to 3 saponifying equivalents, more preferably, 2.1 to 2.9 saponifying equivalents and, much more preferably, 2.2 to 2.7 saponifying equivalents with respect to the fatty acid or the animal/vegetable oil.

Further, a ratio of the sodium hydroxide to the organic amine is preferably from 1:0.8 to 1:2, more preferably from 1:0.9 to 1:1.9 and, still more preferably, from 1:1 to 1:1.8 in molar ratio.

The fatty acid or the animal/vegetable oil used for the transparent soap material according to the present invention may be those generally employed as fundamental sources. As the fatty acid, there can be specifically exemplified stearic acid, lauric acid, myristic acid, palmitic acid and behenic acid and the like. The fatty acid, whether synthetic or natural, may be available. Further, as the animal/vegetable oil, specifically, beef tallow, coconut oil and hydrogenated coconut oil, and the like, which is previously hydrolyzed into the fatty acid, may be used or may be used intact.

Further, a quantity of the fatty acid prepared as a raw material into the transparent soap material according to the present invention, i.e., a preparing quantity of the fatty acid, is preferably from 30% to 60% by weight, more preferably from 35% to 57% by weight and, much more preferably, from 37% to 55% by weight. Moreover, a preparing quantity of triethanolamine is from 30% to 50% by weight, more preferably from 31% to 47% by weight, and even more preferably from 32% to 45% by weight. Furthermore, a preparing quantity of sodium hydroxide is preferably from 5% to 10% by weight, more preferably from 5.5% to 9.5% by weight, and much more preferably from 6% to 9% by weight.

In the transparent soap material according to the present invention, if in such a range as not to spoil the effects of the present invention, there can be optional components generally used for the soap in addition to the indispensable components described above. As the above optional components, there may be exemplified, e.g., antioxidant such as BHT, chelating agent such as EDTA and hydroxyethane diphosphonic acid, antiseptic agent such as methylparaben, coloring matters, pigments, fine particles, mica titanes with interference colors, pearl agent such as mica titanes, perfume, surface active agent such as POE added sodium alkylsulfate, and monovalent or polyvalent alcohol or polysaccharide such as ethanol, glycerine, white saccharide, maltitol, sorbitol and honey and the like.

Note that the transparent solid soap according to the present invention is mixed with the coloring matters, the pigments, the fine particles, the mica titanes with interference colors or the pearl agent and the like as the above optional component, whereby the soap can, though the transparency might be spoiled to some extent depending on an addition quantity, become highly lustrous and conspicuous in color.

The transparent soap material according to the present invention can be manufactured by an ordinary soap material manufacturing method. For example, the transparent soap material of the present invention can be transformed into a pellet, i.e., a solidified soap material obtained by saponifying the fatty acid with alkali, adding other components as the necessity arises, kneading these components, effecting a rolling process and extruding and solidifying them.

Moreover, the transparent solid soap can be obtained by carrying out pellet processing such as pressurization-molding, i.e., by a mechanical kneading method. Further, if pressurization-molded by use of the pellet into which the transparent soap material of the present invention is molded and the pellet manufactured from an ordinary opaque soap material, a transparent solid soap having a stripe pattern is to be obtained. Moreover, a flower-shaped molding is made of an opaque soap and embedded in and wrapped with the transparent soap material of the present invention by the frame kneading method, thereby making it possible to obtain a transparent solid soap with the molding embedded in and wrapped therewith. Further, if a printed thin film composed of carboxymethylcellulose is embedded in and wrapped therewith, it is feasible to obtain the transparent solid soap with a picture drawn inside.

BEST MODE OF CARRYING OUT THE INVENTION

The present invention will hereinafter be described in detail by exemplifying Examples. However, the present invention is not, as a matter of course, limited to only these Examples. Note that numerical values of prescription are parts by weight as far as no particular indications are given.

EXAMPLES 1–6

The transparent soap material is manufactured according to a prescription of Table 1 which follows. Concretely, prescription components in Table 1 are scale-put into a heating kneader, kneaded for 2 hours at 80° C., and, through a pelletizing operation by a hot roll and a pelleter, the transparent soap material is obtained as a pellet. When a moisture content of this pellet is obtained by Karl Fischer moisture content titration, the moisture content of the pellet comes to a result as shown in Table 1. When a component composition of the pellet is calculated from this moisture content, the component composition as shown in Table 2 is obtained. Note that a quantity of alkali with respect to fatty acid is as shown in Table 3.

TABLE 1

| Component | Example 1 | Example 2 | Example 3 | Example 4 | Example 5 | Example 6 |
|---|---|---|---|---|---|---|
| Coconut oil fatty acid | 40 | 40 | 40 | 40 | 40 | 40 |
| Beef tallow fatty acid | 160 | 160 | 160 | 160 | 160 | 160 |
| Triethanolamine | 140 | 145 | 160 | 170 | 175 | 160 |
| Sodium hydroxide | 34 | 29 | 26 | 34 | 26 | 31 |
| Water | 86 | 81 | 79 | 86 | 79 | 84 |
| State of pellet | Transparent solid-state | Transparent solid-state | Transparent solid-state | Transparent solid-state | Transparent solid-state | Transparent solid-state |
| Pellet moisture content (weight %) | 5.4 | 6.2 | 4.8 | 6.1 | 5.5 | 5.6 |

TABLE 2

| Component | Example 1 | Example 2 | Example 3 | Example 4 | Example 5 | Example 6 |
|---|---|---|---|---|---|---|
| Coconut oil fatty acid | 10.2 | 10.0 | 9.7 | 9.3 | 9.4 | 9.7 |
| Beef tallow fatty acid | 40.9 | 40.1 | 39.5 | 37.2 | 37.7 | 38.6 |
| Triethanolamine | 35.8 | 36.4 | 39.5 | 39.5 | 41.3 | 38.6 |
| Sodium hydroxide | 8.7 | 7.3 | 6.4 | 7.9 | 6.1 | 7.5 |
| Water | 4.4 | 6.2 | 4.8 | 6.1 | 5.5 | 5.6 |

TABLE 3

(Unit: Saponifying Equivalent)

| | Alkali quantity to fatty acid |
|---|---|
| Example 1 | 2.37 |
| Example 2 | 2.24 |
| Example 3 | 2.28 |
| Example 4 | 2.65 |
| Example 5 | 2.41 |
| Example 6 | 2.45 |

EXAMPLES 7–12

The transparent solid soap is obtained by pressurization-forming the pellet-like transparent soap material in the Examples 1–6. In this transparent solid soap, a change in weight is less than 5% even when preserved at 40° C. for one month, and, further, neither variation in the transparency nor crystal deposition can be seen.

EXAMPLE 13

The transparent soap material is manufactured according to a scaling prescription in Table 4 which follows. Concretely, the prescription components in Table 4 are scale-put into the heating kneader, kneaded for 2 hours at 80° C., and, through the pelletizing operation by the hot roll and the pelleter, the transparent soap material is obtained as a pellet. Note that according to the prescription in Table 4, the alkali quantity to the fatty acid is 2.45 saponifying equivalents.

A moisture content of this pellet was 5.6% by weight (which is based on the Karl Fischer moisture content titration). This pellet exhibited neither the crystal deposition nor change in the transparency even when preserved at 40° C. for one month.

TABLE 4

(Scaling Prescription)

| Component | Mixing quantity |
|---|---|
| Stearic acid | 30 |
| Palmitic acid | 13 |
| Sodium hydroxide | 6.7 |
| Triethanolamine | 32 |
| BHT | 0.1 |
| Hydroxyethane diphosphonic acid | 0.1 |
| Water | 10.7 |
| Ethanol | 7.4 |

EXAMPLE 14

The transparent solid soap is obtained by pressurization-forming the transparent soap material in the example 13. This transparent solid soap showed neither the variation in the transparency nor crystal deposition even when preserved at 40° C. for one month.

EXAMPLE 15

The transparent soap material is manufactured according to a scaling prescription in Table 5 which follows. Concretely, the prescription components in Table 5 are scale-put into the heating kneader, kneaded for 2 hours at 80° C., and, through the pelletizing operation by the hot roll and the pelleter, the transparent soap material is obtained as a pellet. Note that according to the prescription in Table 5, the alkali quantity to the fatty acid is 2.45 saponifying equivalents.

A moisture content of this pellet was 5.1% by weight (which is based on the Karl Fischer moisture content titration). In this pellet, there was no change in the weight even when preserved at 40° C. for one month.

TABLE 5

(Scaling Prescription)

| Component | Mixing quantity |
|---|---|
| Stearic acid | 30 |
| Palmitic acid | 13 |
| Sodium hydroxide | 6.7 |
| Triethanolamine | 32 |
| BHT | 0.1 |
| Hydroxyethane diphosphonic acid | 0.1 |
| Water | 10.7 |
| Sorbitol | 7.4 |

EXAMPLE 16

The transparent solid soap is obtained by pressurization-forming the transparent soap material in the example 15. This transparent solid soap showed no variation in the weight even when preserved at 40° C. for one month.

EXAMPLE 17

The transparent soap material is manufactured according to a scaling prescription in Table 6 which follows. Concretely, the prescription components in Table 6 are scale-put into the heating kneader, kneaded for 2 hours at 80° C., and, through the pelletizing operation by the hot roll and the pelleter, the transparent soap material is obtained as a pellet. Note that according to the prescription in Table 6, the alkali quantity to the fatty acid is 2.45 saponifying equivalents.

A moisture content of this pellet was 5.1% by weight (which is based on the Karl Fischer moisture content titration). This pellet was a luster white solid body. This soap material showed no variation in the weight even when preserved at 40° C. for one month.

TABLE 6

| (Scaling Prescription) | |
|---|---|
| Component | Mixing quantity |
| Stearic acid | 30 |
| Palmitic acid | 13 |
| Sodium hydroxide | 6.7 |
| Triethanolamine | 32 |
| BHT | 0.1 |
| Hydroxyethane diphosphonic acid | 0.1 |
| water | 17.1 |
| Titanium oxide | 1 |

EXAMPLE 18

The transparent soap material is manufactured according to a scaling prescription in Table 7 which follows. Concretely, the prescription components in Table 6 are scale-put into the heating kneader, kneaded for 2 hours at 80° C., and, through the pelletizing operation by the hot roll and the pelleter, the transparent soap material is obtained as a pellet. Note that according to the prescription in Table 7, the alkali quantity to the fatty acid is 2.45 saponifying equivalents.

A moisture content of this pellet was 5.1% by weight (which is based on the Karl Fischer moisture content titration). This pellet exhibited no change both in the weight and the transparency even when preserved at 40° C. for one month.

TABLE 7

| (Scaling Prescription) | |
|---|---|
| Component | Mixing quantity |
| Stearic acid | 30 |
| Palmitic acid | 13 |
| Sodium hydroxide | 6.7 |
| Triethanolamine | 32 |
| BHT | 0.1 |
| Hydroxyethane diphosphonic acid | 0.1 |
| Water | 18.1 |

EXAMPLE 19

The pellet in the example 17 is molten by heating, poured into a silicone rubber mold and solidified, thus manufacturing a molding of a flower of rose. This molding is placed in a frame, and the transparent soap material molten by heating in the example 18 is softly poured and solidified by cooling, thus obtaining a transparent solid soap including a flower. This transparent solid soap exhibited neither the change in the transparency of the transparent portion nor the change in the weight even when preserved at 40° C. for one month.

INDUSTRIAL APPLICABILITY

The transparent solid soap and the transparent soap material according to the present invention can be easily produced without requiring a fine control of the moisture content and a maturing period till reduction in the weight are settled, and, besides, exhibit the high stabilities of the transparency and of the weight with the passage of time.

What is claimed is:

1. A transparent solid soap obtained by saponifying fatty acid or animal/vegetable oil with alkali, consisting essentially of a salt of fatty acid, wherein 1) said alkali is sodium hydroxide and triethanolamine, and a molar ration of said sodium hydroxide to said organic amine is from 1:0.8 to 1:1.8, and 2) a quantity of said alkali is 2.2 to 2.7 saponifying equivalents to said fatty acid or said animal/vegetable oil.

2. A transparent soap material obtained by saponifying fatty acid or animal/vegetable oil with alkali, consisting essentially of a salt of fatty acid, wherein 1) said alkali is sodium hydroxide and triethanolamine, and a molar ratio of said sodium hydroxide to said organic amine is from 1:0.8 to 1:1.8, and 2) a quantity of said alkali is 2.2 to 2.7 saponifying equivalents to said fatty acid or said animal/vegetable oil.

3. A transparent soap material according to claim 2, wherein said transparent soap material is solidified.

4. A transparent solid soap obtained by molding a transparent soap material according to claim 2.

5. A solid soap shaped into a desired form, consisting essentially of:

a transparent solid soap material obtained by saponifying fatty acid or animal/vegetable oil with an alkali of sodium hydroxide and triethanolamine having a molar ratio of sodium hydroxide to organic amine of 1:0.8 to 1:1.8, said alkali being used in an amount equivalent to a saponifying equivalent of 2.2 to 2.7 for said fatty acid or animal/vegetable oil; and a cosmetically acceptable additive.

6. The solid soap according to claim 5, further comprising a layer of an opaque solid soap material.

7. A method of producing a transparent solid soap material, consisting essentially of:

saponifying fatty acid or animal/vegetable oil with an alkali of sodium hydroxide and triethanolamine having a molar ratio of sodium hydroxide to organic amine of 1:0.8 to 1:1.8, said alkali being used in an amount equivalent to a saponifying equivalent of 2.2 to 2.7 for said fatty acid or animal/vegetable oil; and uniformizing the saponified material.

8. A transparent solid soap consisting essentially of a salt of fatty acid obtained by saponifying fatty acid or animal/vegetable oil with alkali, wherein 1) said alkali is sodium hydroxide and triethanolamine, and a molar ratio of said sodium hydroxide to said organic amine is from 1:0.8 to 1:1.8, 2) a quantity of said alkali is 2.2 to 2.7 saponifying equivalents to said fatty acid or said animal/vegetable oil, and 3) no polysaccharide or alcohol is included.

9. The transparent solid soap according to claim 1, wherein said fatty acid is selected from the group consisting of beef tallow, coconut oil, hydrogenated coconut oil, stearic acid, lauric acid, myristic acid, palmitic acid, behenic acid, and combinations thereof.

10. The transparent soap material according to claim 2, wherein said fatty acid is selected from the group consisting of beef tallow, coconut oil, hydrogenated coconut oil, stearic acid, lauric acid, myristic acid, palmitic acid, behenic acid, and combinations thereof.

* * * * *

UNITED STATES PATENT AND TRADEMARK OFFICE
CERTIFICATE OF CORRECTION

PATENT NO. : 6,462,003 B1
DATED : October 8, 2002
INVENTOR(S) : Isao Shimosato and Masanori Okada It is certified that error appears in the above-identified patent and that said Letters Patent is hereby corrected as shown below:

Title page, Item [54] and Column 1, lines 1 & 2,
The title should be: -- TRANSPARENT SOLID SOAP AND METHOD OF MAKING THE SAME --

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,462,003 B1 
DATED : October 8, 2002
INVENTOR(S) : Isao Shimosato and Masanori Okada It is certified that error appears in the above-identified patent and that said Letters Patent is hereby corrected as shown below:

Column 10,
Line 2, “ration” should be changed to -- ratio --

Signed and Sealed this

Twenty-second Day of July, 2003

JAMES E. ROGAN
*Director of the United States Patent and Trademark Office*